(12) United States Patent
Boyd

(10) Patent No.: US 8,801,745 B2
(45) Date of Patent: *Aug. 12, 2014

(54) METHODS AND DEVICES FOR REMOVING MATERIAL FROM A VASCULAR SITE

(75) Inventor: Stephen W. Boyd, Moss Beach, CA (US)

(73) Assignee: Covidien LP, Mansfield, MA (US)

( * ) Notice: Subject to any disclaimer, the term of this patent is extended or adjusted under 35 U.S.C. 154(b) by 1442 days.

This patent is subject to a terminal disclaimer.

(21) Appl. No.: 10/625,145

(22) Filed: Jul. 22, 2003

(65) Prior Publication Data

US 2005/0090845 A1    Apr. 28, 2005

Related U.S. Application Data

(63) Continuation of application No. 09/507,339, filed on Feb. 18, 2000, now Pat. No. 6,629,953.

(51) Int. Cl.
*A61M 29/00* (2006.01)

(52) U.S. Cl.
USPC .......................................... 606/200; 604/96.01

(58) Field of Classification Search
USPC ................ 606/110, 113–115, 159, 198, 200; 604/96.01, 104, 106
See application file for complete search history.

(56) References Cited

U.S. PATENT DOCUMENTS

| | | | | |
|---|---|---|---|---|
| 3,320,957 A | * | 5/1967 | Sokolik | 606/180 |
| 5,100,423 A | * | 3/1992 | Fearnot | 606/159 |
| 5,211,651 A | * | 5/1993 | Reger et al. | 606/159 |
| 5,776,141 A | * | 7/1998 | Klein et al. | 623/1.11 |
| 5,888,201 A | * | 3/1999 | Stinson et al. | 623/1.2 |
| 6,156,046 A | * | 12/2000 | Passafaro et al. | 606/159 |
| 6,179,859 B1 | * | 1/2001 | Bates et al. | 606/200 |
| 6,187,025 B1 | * | 2/2001 | Machek | 606/200 |
| 6,196,963 B1 | * | 3/2001 | Williams | 600/3 |
| 6,245,012 B1 | * | 6/2001 | Kleshinski | 623/1.11 |
| 6,263,236 B1 | * | 7/2001 | Kasinkas et al. | 604/21 |
| 6,277,138 B1 | * | 8/2001 | Levinson et al. | 606/200 |
| 6,383,195 B1 | * | 5/2002 | Richard | 606/114 |
| 6,629,953 B1 | * | 10/2003 | Boyd | 604/106 |

\* cited by examiner

*Primary Examiner* — Victor Nguyen
(74) *Attorney, Agent, or Firm* — Alana T. Bergman, Esq.

(57) ABSTRACT

An expandable cage is expanded within a narrowed region of a blood vessel. The expandable cage has openings therein so that plaque protrudes through the openings when the cage is expanded. A material removing element passes within the cage to remove the plaque extending into the openings. The openings are preferably formed by integrally formed elements which provide a smooth internal surface. The material removing element passes along the smooth internal surface when removing the plaque. A collection bag is coupled to the material removing element to capture the material which has been removed.

11 Claims, 18 Drawing Sheets

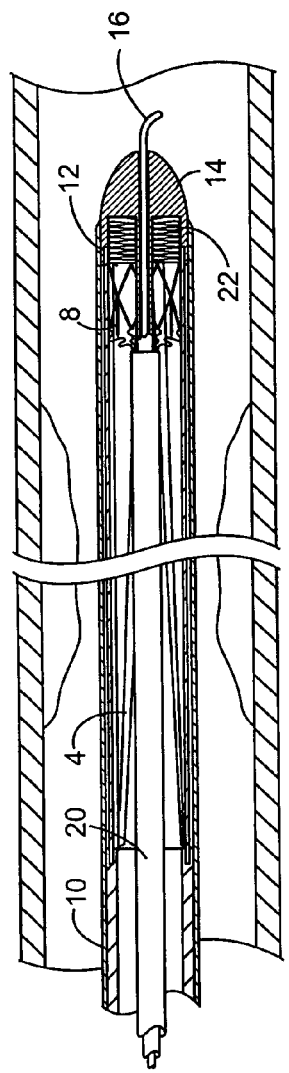
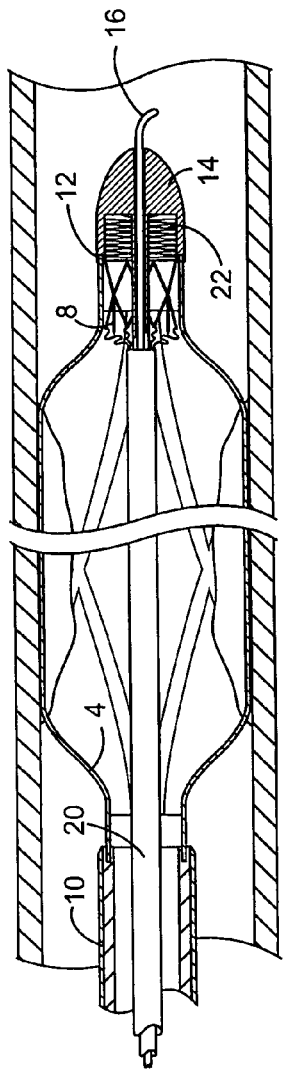
FIG. 5
FIG. 6

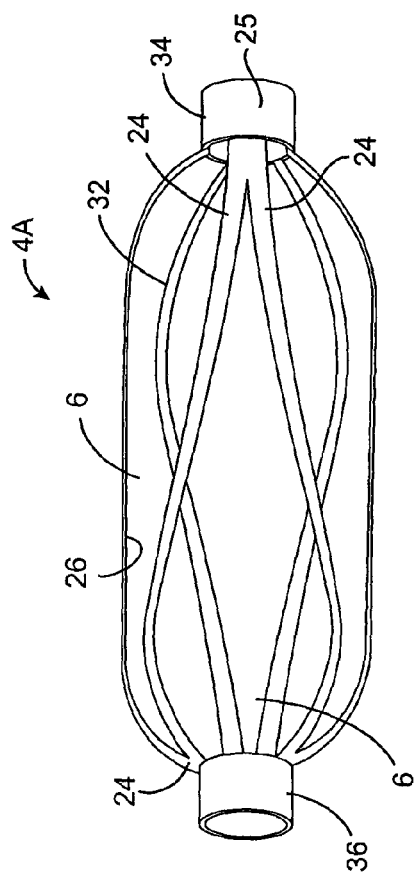
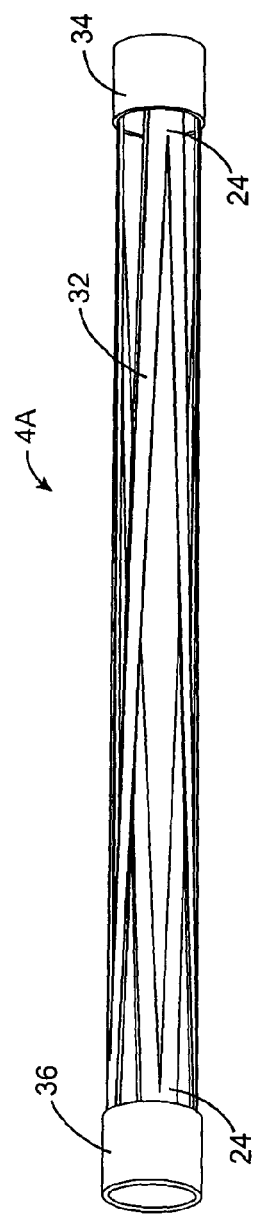
FIG. 14A
FIG. 14B

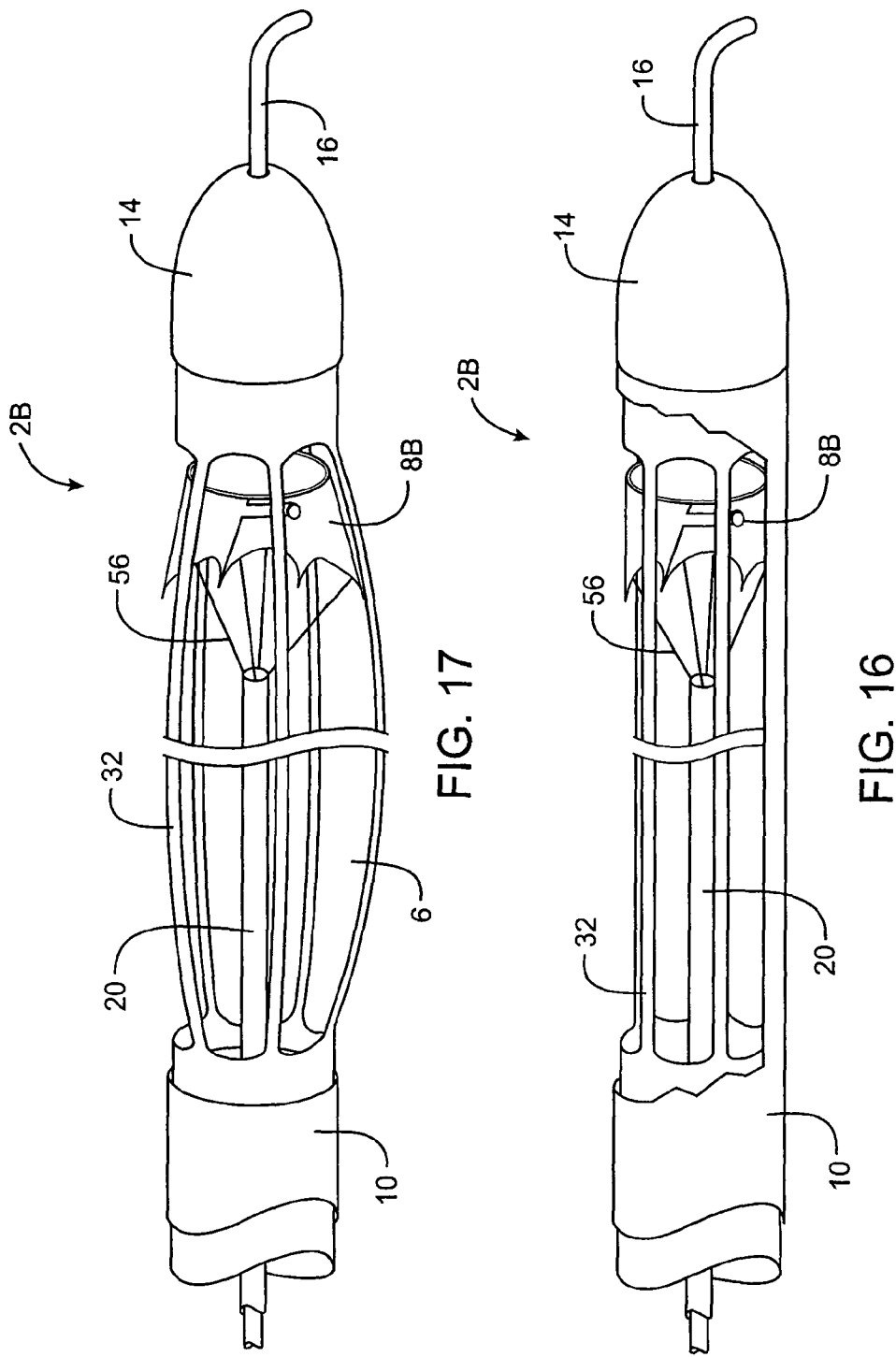

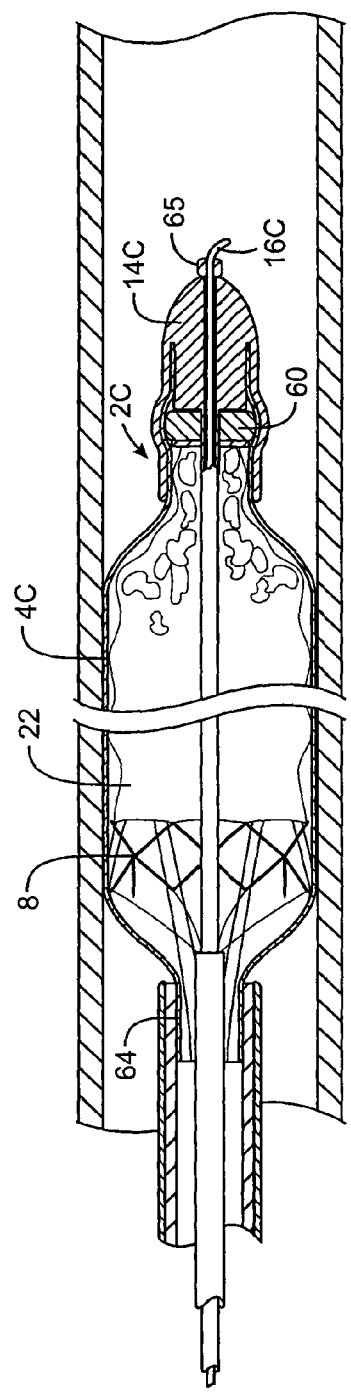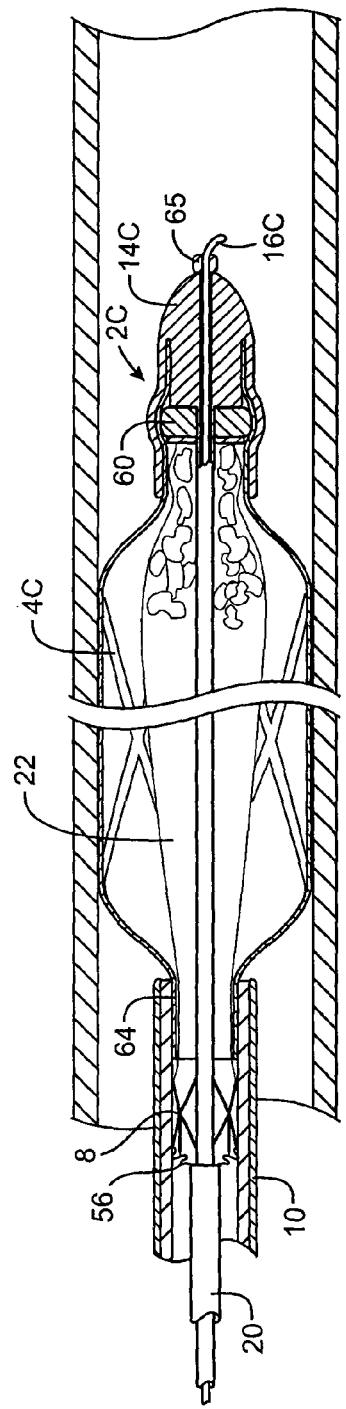

_US 8,801,745 B2_

METHODS AND DEVICES FOR REMOVING MATERIAL FROM A VASCULAR SITE

The present application is a continuation of U.S. patent application Ser. No. 09/507,339 now U.S. Pat. No. 6,629,953, filed Feb. 18, 2000, the full disclosure of which is incorporated herein by reference.

BACKGROUND OF THE INVENTION

The present invention is directed to methods and devices for removing material in procedures such as atherectomy and endarterectomy. Atherectomy, for example, is performed to remove plaque from blood vessels to open obstructed vessels and improve blood flow.

The present invention is directed to improved devices and methods for removing material from a vascular site.

SUMMARY OF THE INVENTION

The present invention provides devices and methods for removing material from a vascular site. The device has an expandable cage which forms a number of openings when expanded. The cage is expanded at the desired site for removing material so that unwanted material extends into the openings. A material removing element is then used to remove material extending into the openings.

The openings in the cage are preferably formed by rigidly connected elements which form a frame around the openings. The rigid frame elastically deforms when the cage is collapsed so that upon release of the collapsed cage, the elastic response of the cage urges the material into the openings. The cage is preferably made of integrally formed elements and may be made of stainless steel or a superelastic material. The cage is preferably held in the collapsed position by a sheath which is retracted to expose the cage and permit the cage to expand. Although the sheath is a preferred structure to collapse the cage, any other structure may be used. The cage may also be expanded utilizing the shape memory characteristics of a shape memory material. The cage may also be vibrated using an ultrasound generator to help the cage penetrate the material to be removed In an aspect of the invention, the cage preferably forms 2-20 openings, more preferably 4-8 openings, which are spaced around the device. An advantage of the present invention is that the user does not need to rotate the device to orient a single cutting window. The openings preferably have a size of at least 0.5 mm$^2$ when expanded and have a length of at least 0.040 inch. The size of the opening is defined by the surface area of an imaginary surface extending between the rigidly connected elements. The length is the longest distance within the opening when measured in the direction of the longitudinal axis of the device. The preferred size and number of openings is particularly suited for atherectomy in the coronary arteries, however, other configurations and sizes may be used without departing from the scope of the invention.

The material removing element may remove the material with any suitable method and a preferred method is to cut the material. The expanded shape of the material removing element is preferably larger than the expanded inner surface of the cage so that the material removing element is urged against the interior surface of the cage. The material extending into and through the openings is sheared by shearing surfaces on the cage and removal element. The material removing element preferably removes material around a significant portion of the cage but may also selectively remove material extending into the openings.

In still another aspect of the present invention, the device may also have a flexible bag which receives the material which has been removed. The bag is preferably attached to the material removing element so that the bag is deployed behind the removing element as the removing element is advanced through the cage. The device may also simply trap the material within the cage and/or material removing element, rather than using the bag, or may use a suction lumen or a capsule in the tip or shaft to trap the material. Thus, although it is preferred to use the bag, any other method of retrieving the material may be used without departing from the scope of the invention.

In accordance with a method of the present invention, an expandable cage is introduced into a vessel. The method is described in connection with the preferred embodiments, however, the method may be practiced with other devices without departing from the scope of the invention. The cage is expanded within the vessel so that material to be removed, such as plaque, extends into the openings. The material removing element is then used to remove the material. The cage protects healthy tissue by limiting the amount of material which is removed. The cage also preferably guides movement of the material removing element, however, this feature may not be essential depending upon the particular removal method used.

In yet another aspect of the invention, the present invention is also directed to a method of removing neo-intimal tissue and other material from the inside of a previously deployed stent. The present invention is particularly useful for this procedure since the cage prevents the material removing element from contacting the stent.

In still another aspect of the present invention, the cage is left within the vessel to hold the vessel open after the procedure.

These and other advantages of the invention will become apparent from the following description, drawings and claims.

BRIEF DESCRIPTION OF THE DRAWINGS

FIG. 5 shows the device positioned at a vascular site where material is to be removed.

FIG. 6 shows the device expanded so that the material protrudes through the openings.

FIG. 14A shows the cage in a collapsed position.

FIG. 14B shows the cage in an expanded position.

FIG. 16 shows the device of FIGS. 12 and 13 with the sheath partially cut-away to show the collapsed cage.

FIG. 17 shows the cage of FIG. 16 expanded.

FIG. 24 shows the device of FIG. 23 with the cage expanded and the material removing element advanced to remove material extending through the openings in the cage.

FIG. 25 shows the material removing element collapsed.

DESCRIPTION OF THE PREFERRED EMBODIMENTS

Figure 1:
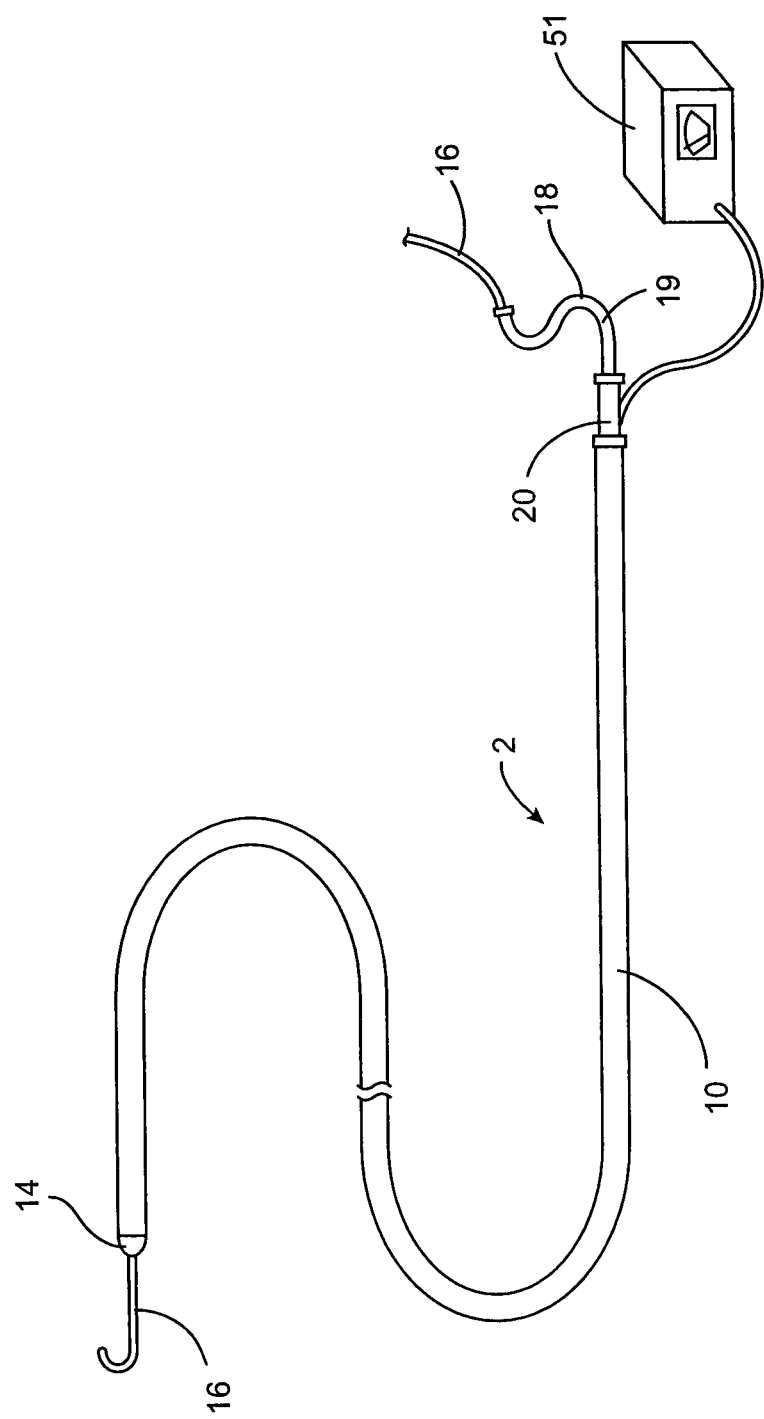
FIG. 1 is an external view of a device of the present invention.

Referring to FIGS. 1-6, a device 2 for removing material from a vascular site is shown. The device 2 is particularly useful for removing plaque from coronary arteries but may be used in any other part of the body without departing from the scope of the invention. The device 2 includes an expandable cage 4 which is movable from the collapsed shape of FIG. 5 to the expanded shape of FIGS. 2, 3 and 6. The cage 4 forms a number of openings 6, preferably 2-10 and more preferably 3-8, in the expanded condition. A material removing element 8 removes material extending into the openings 6.

The openings 6 are relatively large so that the material to be removed can extend into the openings 6 when the cage 4 is expanded. Specifically, the openings 6 preferably have a size of at least 0.25 mm$^2$, and more preferably at least 0.5 mm$^2$, when the cage 4 is expanded. Stated another way, the openings 6 preferably have a size of 0.25-8 mm$^2$ and more preferably 0.5-5 mm$^2$. The openings 6 also extend longitudinally for a length of at least 0.5-10 mm and more preferably 1-5 mm. The size of the opening 6 is defined by the surface area of an imaginary surface extending across the opening 6 and the length is the longest distance within the opening 6 when measured in the direction of a longitudinal axis 11 of the device 2 when the cage 4 is expanded.

Figure 2:
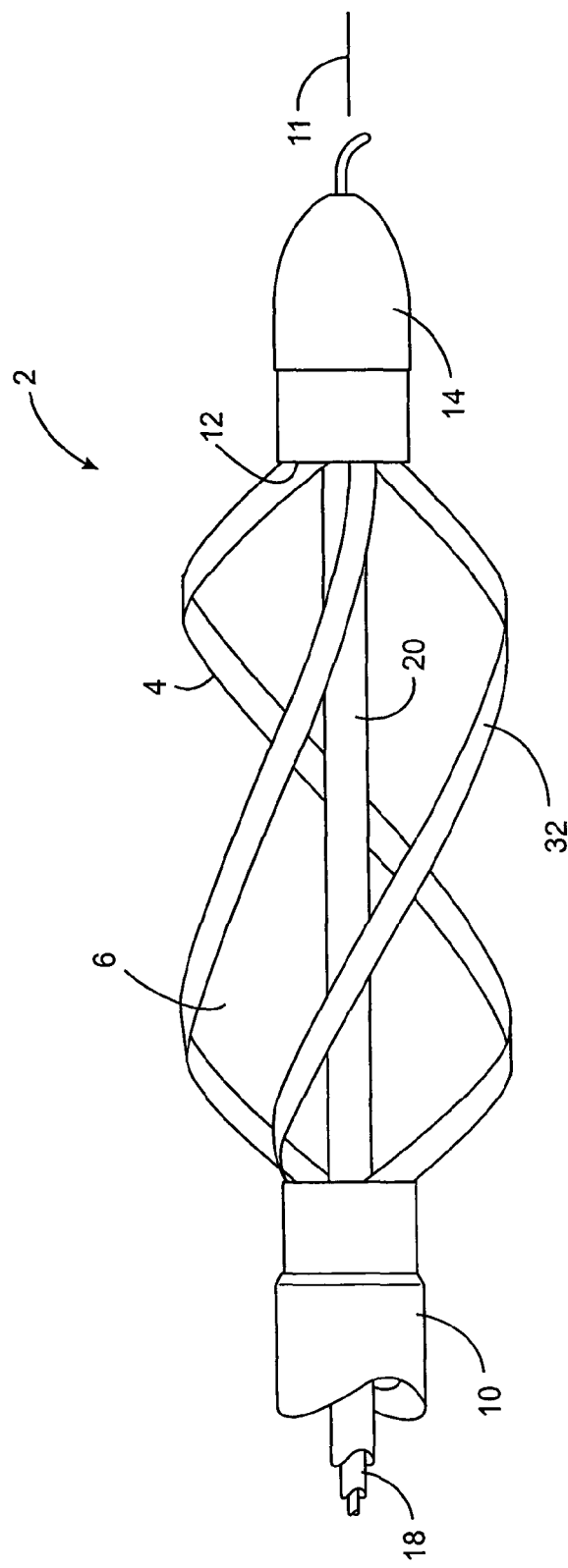
FIG. 2 shows the distal end of the device with a sheath retracted to expose a cage.
Figure 3:
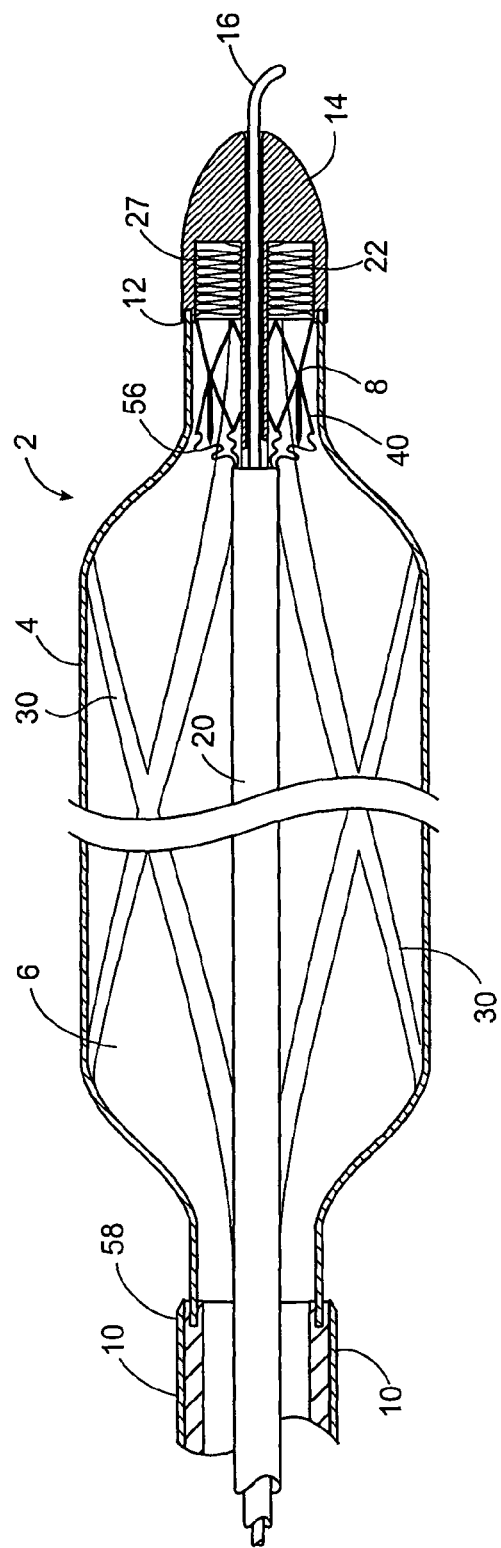
FIG. 3 is a cross-sectional view of the device of FIG. 2.
Figure 4:
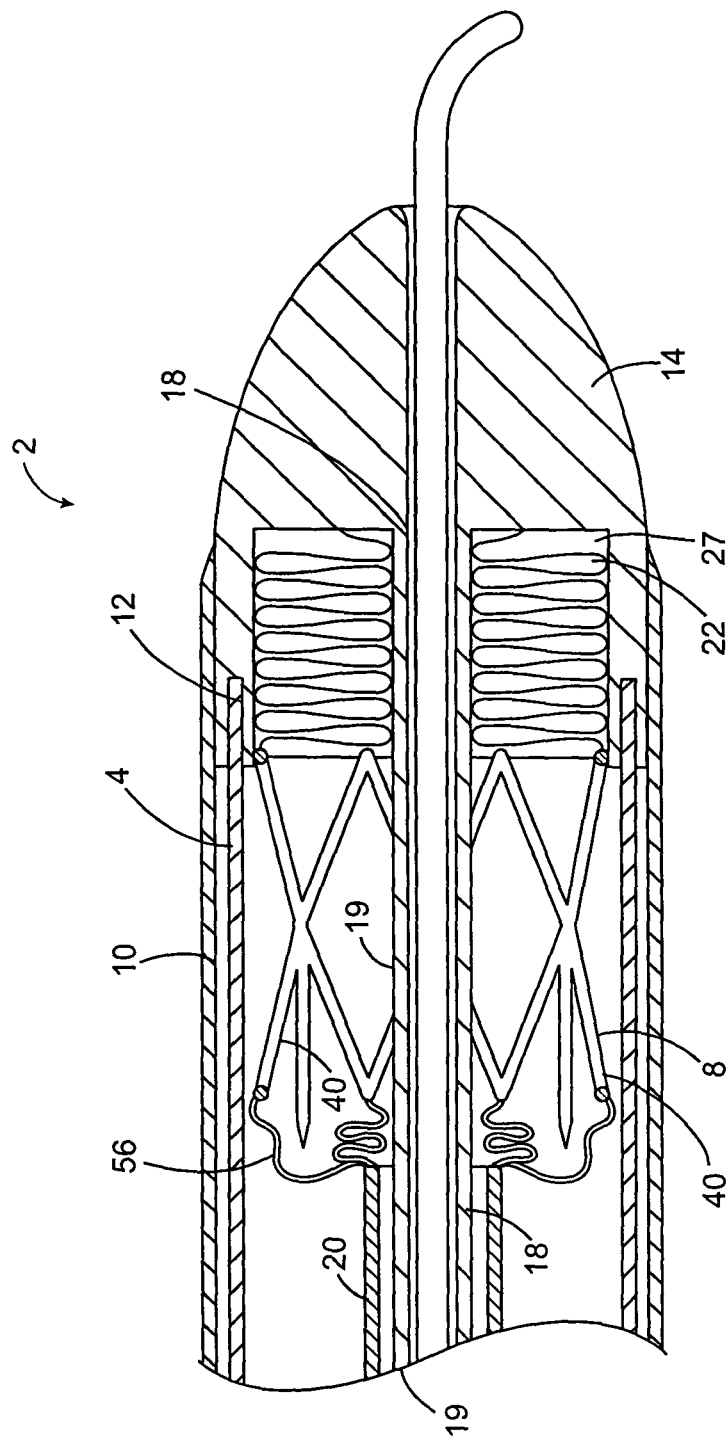
FIG. 4 is an expanded view of the distal end of the device of FIG. 2.
Figure 7:
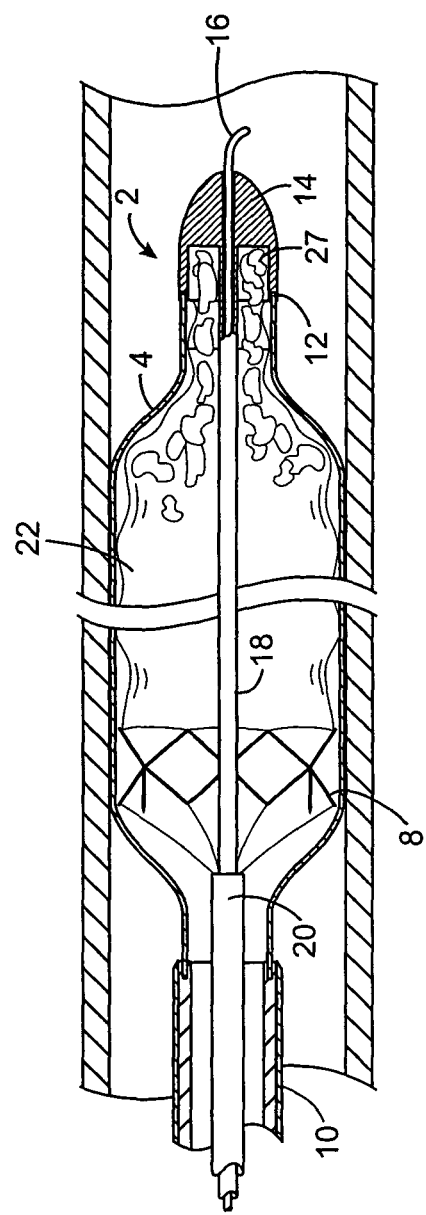
FIG. 7 shows the material removing element moved through the cage so that material is caught by a bag attached to the cage.

The cage 4 is preferably held in the collapsed position by a sheath 10 although any other suitable structure may be used to hold the cage 4 in the collapsed position. The sheath 10 is retracted to expose the cage 4 and permit the cage 4 to expand. The sheath 10 is preferably a tube 58 having a 3-6 F size and is preferably about 4 F so that the device 2 can be advanced through a guide catheter (not shown) of 10 F or less and preferably less than 8 F and most preferably about 6 F. A suitable material for the sheath 10 is HDPE, polyimide or PTFE although any suitable material may be used. The sheath 10 is retracted to expose the cage 4 and permit the cage 4 to expand as shown in FIGS. 2 and 3. The sheath 10 can also be advanced to collapse the cage 4.

A distal end 12 of the cage 4 is attached to a tip 14 having a rounded, atraumatic end. The device 2 is preferably advanced over a guidewire 16 received in a lumen 18 formed by a tube 19. The tube 19 is preferably attached to the tip 14 and may be integrally formed with the tip 14. The proximal end of the cage 4 is attached to a shaft 20 with tethers 56. The material removing element 8 moves through the cage 4 by pulling on the shaft 20 so that the flexible tethers 56 pull the element 8 through the cage 4. The tethers 56 may be rigidly connected to the element 8 or may be tied to the element 8.

A collapsible bag 22 is contained within a chamber 27 in the tip 14. The bag 22 traps material removed by the material removing element 8. The bag 22 is attached to the material removing element 8 so that the bag 22 is deployed as the material removing element 8 is moved through the cage 4. The other end of the bag 22 is attached to the tip 14. The bag 22 may be a porous tube or woven bag 22 and is preferably made of urethane or a woven synthetic fabric. As mentioned above, the bag 22 is a preferred device for trapping the material, however, any other device or method may be used without departing from the scope of the invention. For example, the material may be packed in the shaft, tip or contained entirely within the cage 4 and/or the material removing element 8.

Referring to FIGS. 14A and 14B, the cage 4A has rigidly connected elements 24 which form the openings 6. The cage 4A of FIGS. 14A and 14B may, of course, be used substituted for any other cage described herein and only the cage is shown in FIGS. 14A and 14B for clarity. The rigidly connected elements 24 are deformed, preferably within the elastic range of the material, which includes the superelastic range of a superelastic material, when collapsed. An advantage of the cages 4, 4A of the present invention is that the outward force of the cage 4, 4A urges the material into the openings 6. Another advantage of using the self-expanding cage 4, 4A is that the cage 4, 4A can be designed to produce a desired expansion force. The cage preferably produces a radial opening force of 0.1-1 lb when in the collapsed position. The ability to select and design the opening force of the cage 4 can provide an advantage over devices which develop an opening force with remotely controlled actuators. Such devices may not provide sufficient feedback at the proximal end to properly control the force exerted by the cage. In addition, the ability to design different expansion diameters with different forces allows the user to treat body lumens of different sizes and different atherosclerotic tissue composition.

The rigidly connected elements 24 are preferably integrally formed by a single piece of metal 25 with the openings 6 being cut or etched. The openings 6 are preferably formed by laser cutting or photochemically etching a tube, however, any other suitable method may be used. The tube preferably has a thickness of 0.002-0.005 inch, preferably about 0.003 inch, and is made of a superelastic material or stainless steel although any other suitable material may be used. When the device 2 is used for atherectomy, the cage 4 preferably expands to a diameter of at least 2 mm and preferably about 2-5 mm. The rigidly connected elements 24 form a smooth inner surface 30 so that the material removing element 8 slides along the inner surface 30. The cage 4 also guides the material removing element 8 and controls expansion of the material removing element 8.

Figure 15:
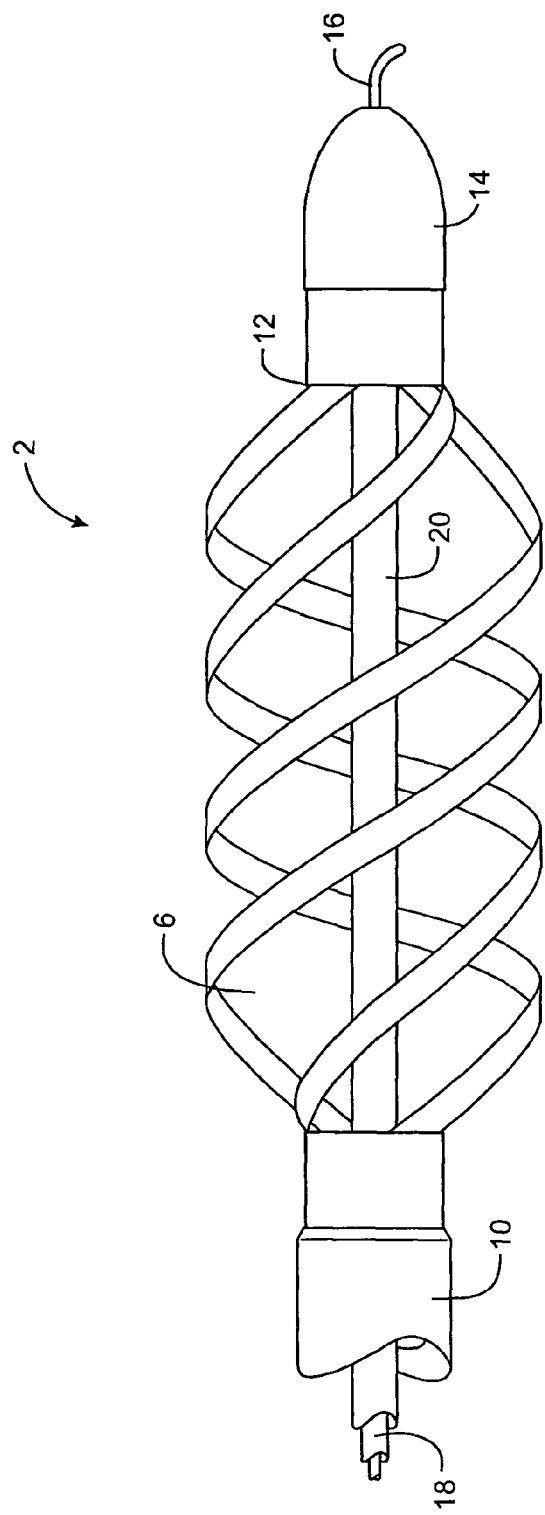
FIG. 15 shows still another cage.

The rigidly connected elements 24 may take any form and a few preferred embodiments are now described below although numerous other shapes may be used without departing from the scope of the invention. Referring to the preferred embodiment of FIGS. 2, 3 and 14A and 14B, the cage 4A has helical columns 32 attached to collars 34, 36 at each end. The collars 34, 36 are attached to the tip 14 and shaft 20. The columns 32 may also be directly attached to the tip 14 or integrally formed with the tip 14 and/or shaft 20 without departing from the scope of the invention. FIG. 14A shows the cage 4A in the collapsed position for clarity, although the cage 4A would normally be in the expanded shape when not restrained by the sheath 10. The cage 4A preferably has 4-20 columns 32 and more preferably about 8-10 columns 32 which are distributed evenly around the cage 4. The columns 32 form an angle with the collars 34, 36 of about 20-90 degrees and preferably about 60-90 degrees in the collapsed position. Referring to FIG. 15, the columns 32 may wrap around the longitudinal axis from 90-360 degrees. The columns 32 of FIG. 15 form helical openings.

Figure 8:
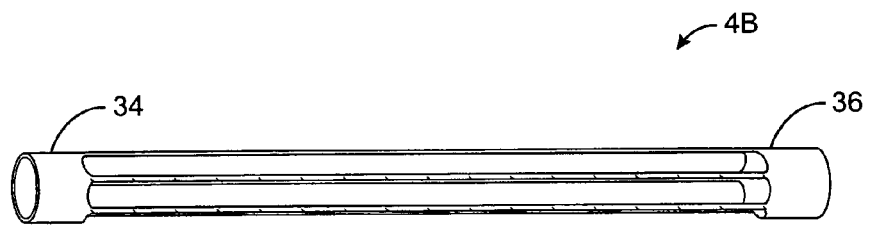
FIG. 8 shows an alternative cage.
Figure 9:
FIG. 9 shows yet another cage.
Figure 10:
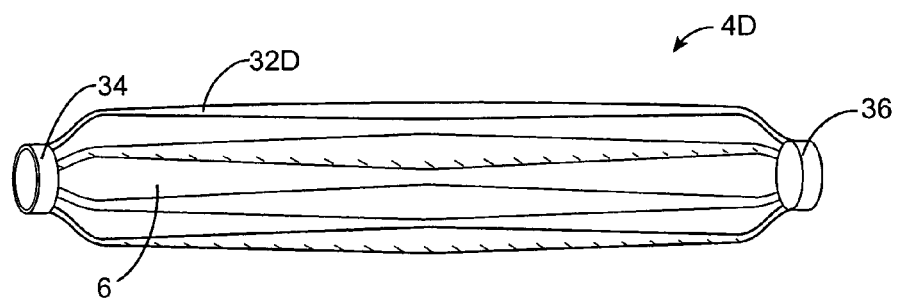
FIG. 10 shows the cage of FIG. 9 in an expanded position.

A few more embodiments of the cage are now described where the same or similar reference numbers refer to the same or similar structure. Referring to FIG. 8, another cage 4B is shown which has axially extending columns 32B forming longitudinally extending openings 6A. The cage 4B may be a superelastic or stainless steel tube having a thickness of about 0.004 inch. Referring to FIG. 9, another cage 4C is shown which has columns 32C with increased width toward the middle of the columns 32C. Referring to FIG. 10, the cage 4C is shown expanded. An advantage of providing the wider columns 32C near the middle is that the columns 32C form a flatter expanded shape and also provide increased stiffness to resist distortion. All cages described herein may share the same attributes such as size, number and length, as all other cages described herein. All the cages described herein may possess a number of cross elements connecting the columns to prevent distortion without departing from the scope of the invention.

The material removing element 8 may remove material by any suitable method such as RF, ultrasound, rotating blades, a cutting element, a drilling element, a high frequency vibrating cutting element, or microwave. The material removing element 8 is preferably part of the device 2 but may also be completely independent from the device 2 and cage 4. Furthermore, the material removing element 8 preferably removes material around the entire inner surface 30 of the cage 4. The material removing element 8 may also remove specific areas without departing from the scope of the invention.

Referring to FIGS. 3-7 and 11, the preferred material removing element 8 cuts the material. The element 8 has cutting surfaces 40 which cooperate with shearing surfaces 42 on the cage 4 to remove the material. A number of teeth 45 and posts 46 are laser-machined or chemically-etched from a stainless steel or superelastic tube. The teeth 45 may or may not be necessary depending upon the atherosclerotic tissue composition, the configuration of the outer element and the resultant shearing force vectors and the addition or deletion of ultrasonic, RF or microwave energy. The element 8 preferably has diamond shaped openings 47 but may be formed in any other manner. The material removing element 8 preferably has an expanded shape which is larger than the internal shape of the expanded cage 4. In this manner, the element 8 is urged against the inner surface 30 of the cage 4 to develop a shearing action with the cage 4. Such a configuration also provides additional force to open the cage 4 and force material through the openings 6 as the element 8 is advanced through the cage 4. The element 8 may also engage the cage with slots or other suitable structure.

Figure 12:
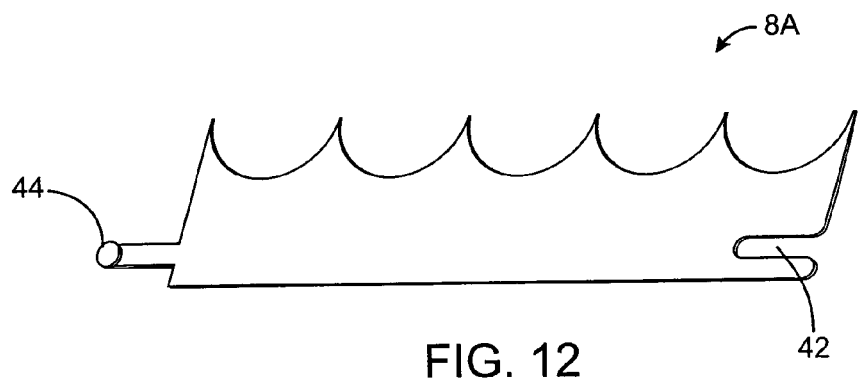
FIG. 12 shows another material removing element which can be formed from a sheet of material.
Figure 13:
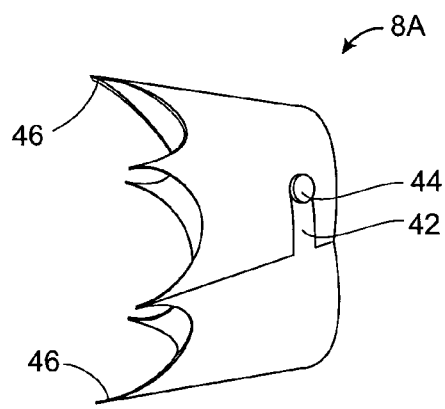
FIG. 13 shows the material removing element of FIG. 12 folded to form a tubular structure.

Referring to FIGS. 12 and 13, another material removing element 8A is shown. The element 8A has a slot 42 and a pin 44 which engage one another. The pin 44 and slot 42 cooperate to permit the element 8A to circumferentially expand and collapse as guided by the slot 42 and pin 44. The element 8A may be formed from a flat sheet of material, such as a superelastic material, which is cut, ground or etched into the shape shown in FIG. 12. The slot 42 and pin 44 are then engaged to form a tubular structure. The element 8A has a number of teeth 46 to cut through the material. The element 4A is preferably flared outwardly toward the teeth 46 so that the teeth 46 maintain contact with the cage 4, 4A (FIGS. 2 and 8) when advanced through the cage 4, 4A.

Figure 18:
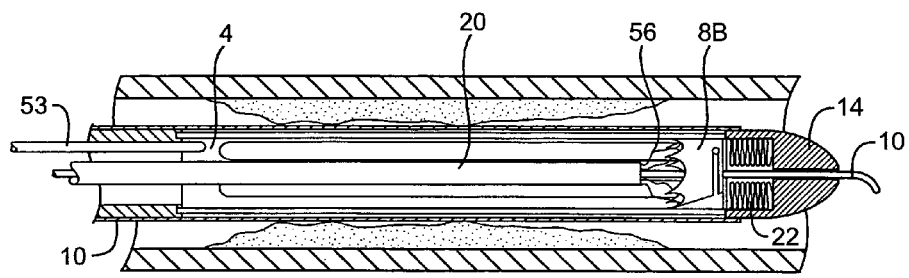
FIG. 18 shows the device of FIG. 17 advanced to a vascular site.
Figure 19:
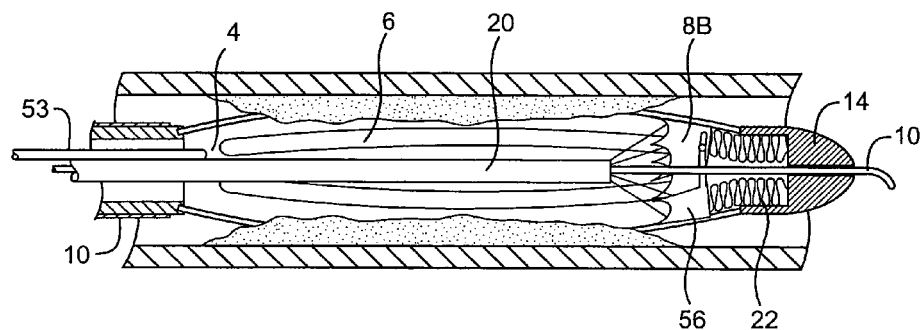
FIG. 19 shows the device of FIG. 18 expanded so that material extends through the openings.
Figure 20:
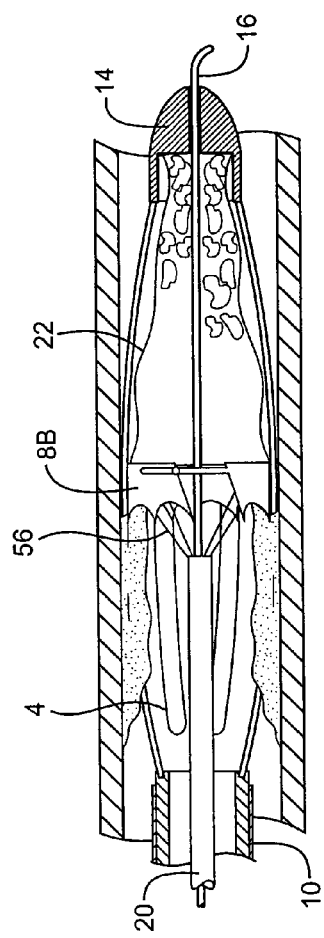
FIG. 20 shows the material removing element advanced halfway through the cage and the material trapped in the bag.
Figure 21:
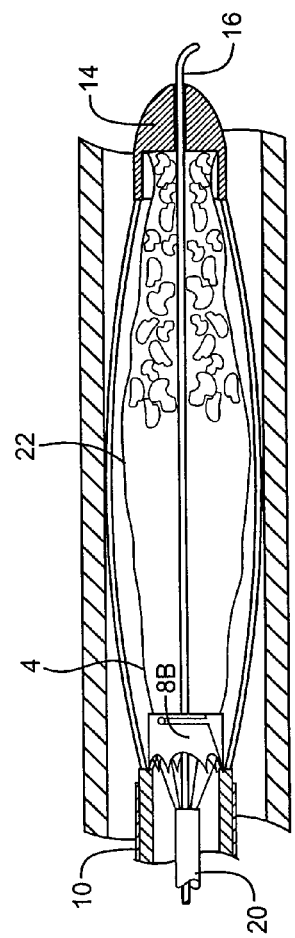
FIG. 21 shows the material removing element advanced completely through the cage.

Referring to FIGS. 16 and 17, another device 2B is shown with the material removing element 8B and the cage 4B where the same or similar reference numbers refer to the same or similar structure. Referring to FIG. 18, the device 2B is advanced to a vascular site where material is to be removed. The material removing element 4B is then moved through the cage 4B to remove the material as shown in FIG. 19. The material is trapped in the bag 22 in the manner shown in FIGS. 20 and 21.

Figure 22:
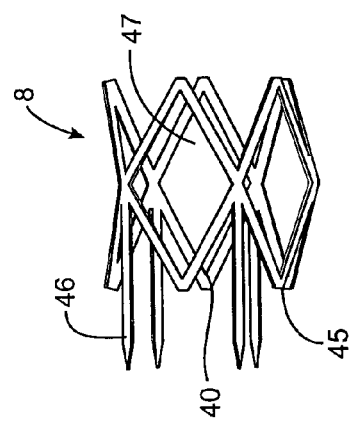
FIG. 22 shows another material removing element.
Figure 11:
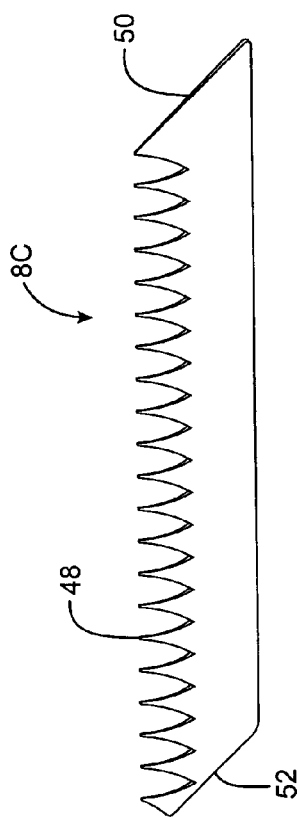
FIG. 11 shows the material removing element.
Figure 23:
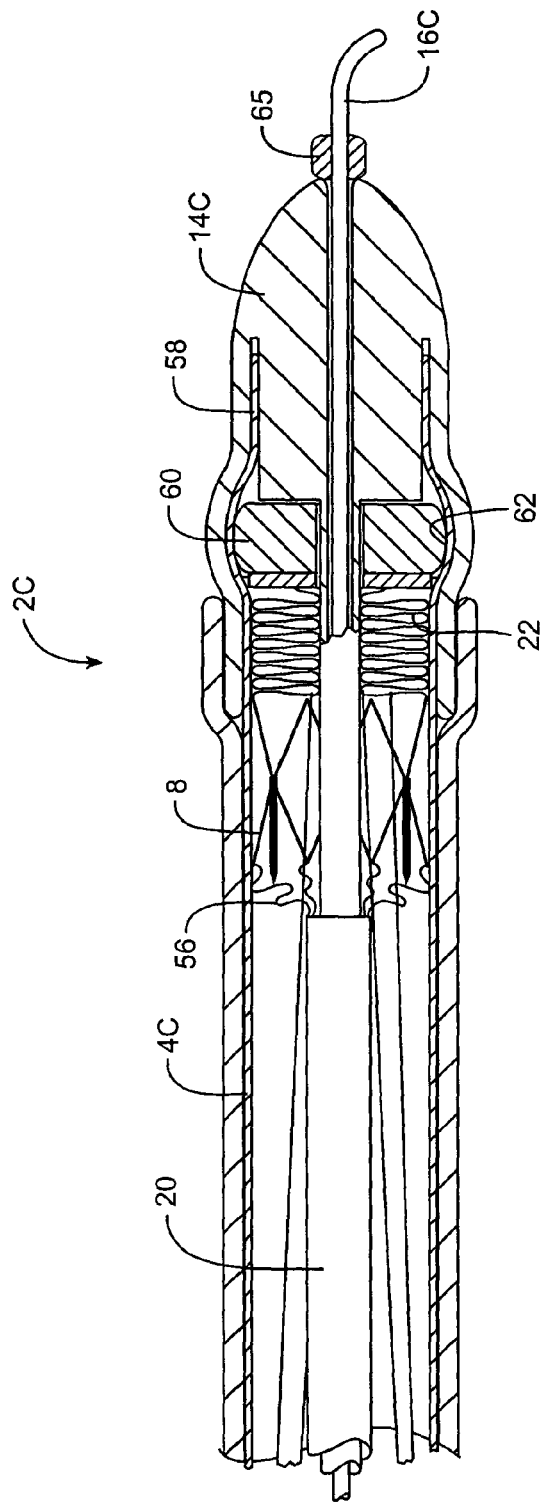
FIG. 23 shows another device for removing material from a vascular site.

Referring to FIG. 22, yet another element 8C is shown which has teeth 48 to cut and remove the material. The element 8C is folded into a tube (not shown) with angled ends 50, 52 sliding against one another when the element 8C expands and collapses. The element 8B may be formed with any suitable materials and is preferably formed with a superelastic material. The ends 50, 52 form an angle of about 40 degrees and have a length of about 0.059 inch.

Referring again to FIGS. 1 and 18, any of the cages or material removing elements described herein may be coupled to an ultrasound generator 51. The ultrasound generator is activated to vibrate the cage 4 during deployment and/or during advancement of the material cutting element 8. The ultrasound generator 51 sends ultrasonic vibrations to the cage 4 with a waveguide 53 oscillating at preferably 10-30 MHz to aid in deployment and tissue removal. The ultrasound generator 51 may also be coupled to the guidewire 16 to help advance the guidewire through the vasculature and, in particular, through narrowed regions in the vasculature.

Use of the devices 2, 2A, 2B is now described. Although the preferred embodiments show specific cages 4, 4A, 4B and material removing elements 8, 8A, 8B, 8C the present invention may, of course, be practiced with other suitable structures without departing from the scope of the invention. The device 2 is advanced to the site to be treated over the guidewire 16. When the device 2 is at the desired treatment site, the sheath 10 is retracted to expose the cage 4 and permit the cage 4 to expand. As the cage expands, material enters the openings 6. The material removing element 8 is then advanced through the cage 4 to remove the material. As mentioned above, the material removing element 8, cage 4 or guidewire 16 may be vibrated using the ultrasound generator to help in advancing the device and removing the material. The material removed by the element 8 is contained within the bag 22. The element 8 is then pulled further so that the proximal end of the cage 4 collapses the element 8. The sheath 10 is then advanced over the cage to collapse the cage 4 and the device 2 is then removed.

Referring to FIGS. 23-28, another device 2C for removing and displacing material from a vascular site is shown where the same or similar reference numbers refer to the same or similar structure. The device 2C is used in a similar manner to the devices described above and all advantages, features, dimensions and combinations described above are equally applicable here.

Figure 28:
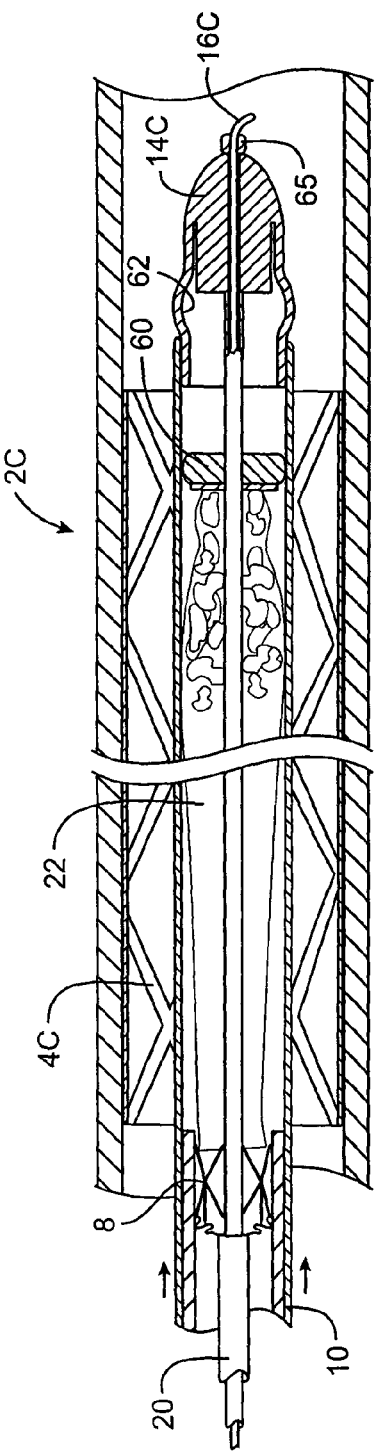
FIG. 28 shows the sheath advanced over the bag.

The device 2C has a cage 4C which is deployable within the vasculature as shown in FIG. 28. The cage 4C may be deployed before the element 8 is advanced or after the element 8 has been used a number of times. When the cage 4C is deployed, the cage 4C holds the vessel open in much the same manner as a stent.

A distal end 58 of the cage 4C is trapped between the tip 14C and a plug 60. The tip 14C has a recess 62 which receives the plug 60 and the cage 4C. The plug 60 is moved out of the recess 62 to release the distal end 58 of the cage 4C. The plug 60 is attached to the bag so that the plug 60 is released from the recess 62 by manipulating the bag 22 as described below. A proximal end 64 of the cage 4C is simply contained within the sheath 10 and is released when the sheath 10 is retracted far enough. The guidewire 16C may have a radiopaque marker band 65 to stabilize the tip 14C when releasing the cage 4C.

Figure 26:
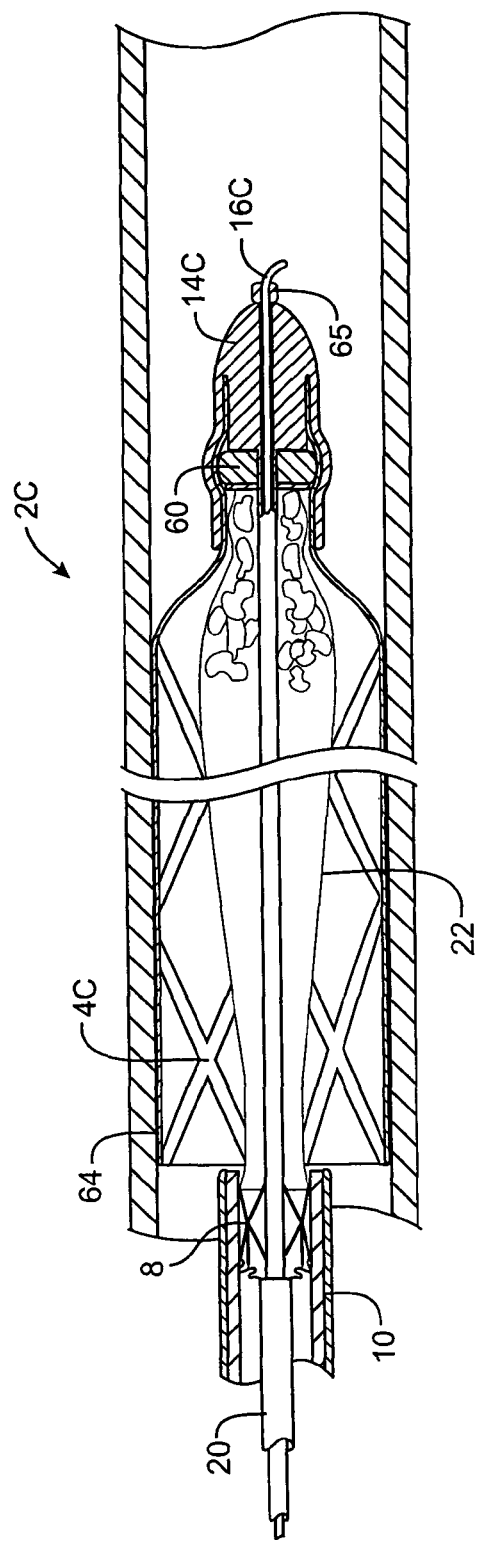
FIG. 26 shows a proximal end of the cage released.
Figure 27:
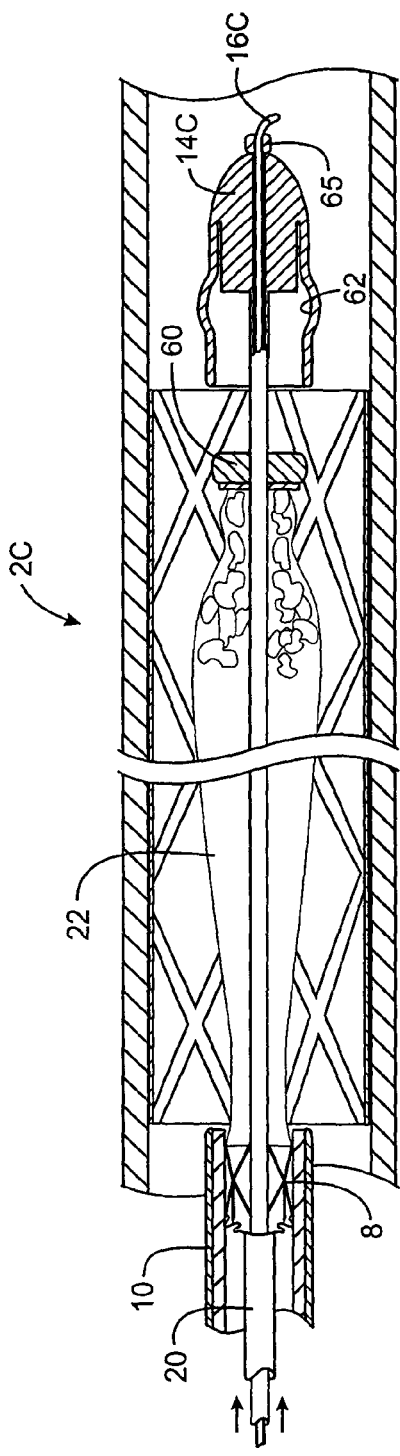
FIG. 27 shows a distal end of the cage released to release the cage.

Use of the device 2C is now described. The device 2C is introduced into the patient, advanced to a vascular site, the sheath 10 is retracted to permit the cage 4 to expand, and the element 8 is moved through the cage 4 to remove material which is trapped in the bag 22 as shown in FIG. 24. The element 8 is moved further to collapse the element 8 as shown in FIG. 25. The proximal end of the cage 4C is then released by simply retracting the sheath further as shown in FIG. 26. The distal end of the cage is released by pulling the plug to release the plug from the recess. The sheath is then advanced over the bag 22 to trap the bag 22 in the device 2C as shown in FIG. 27. The device 2C is then removed leaving the cage 4C in place. The cage may, of course, be deployed at a site other than the site where the material was removed. Furthermore, the material removing element may be used a number of times before deploying the cage so that material may be removed at a number of vascular sites before the cage is deployed. As described above, the material removing element may remove material in some other fashion other than cutting and the material may be trapped in any other manner without departing from the scope of the invention.

While the above is a description of the preferred embodiments of the invention, various alternatives, substitutions and modifications may be made without departing from the scope thereof, which is defined by the following claims. Thus, the preferred embodiments should not be taken as limiting the scope of the invention. For example, the cage may also provide vascular brachytherapy. Furthermore, the present invention is directed to a number of separate inventions and each of these inventions may be claimed independently of one another. Each feature, aspect and advantage of the invention may be claimed independent of one another without departing from the scope of the invention. For example, the size and number of openings is a feature independent of the fact that the cage opens automatically and both of these features may be independent from the fact that the cage is preferably formed with integrally formed elements. Thus, the invention does not include a single essential feature, aspect or advantage and the invention should not be limited as such.

What is claimed is:

1. A device for removing material from a vessel wall at a vascular site, comprising:
   a cage which is movable from a collapsed position to an expanded position, the cage having a plurality of openings in the expanded position, the openings being formed by rigidly connected elements, the cage being configured such that when the cage is in the expanded position at the vascular site material from the vessel wall extends from the vessel wall into the openings, the cage having an inner surface which defines a cavity, the cage being releasable so that the cage may be left within the patient; and
   a material removing element positioned within the cage cavity to remove the material from the vessel wall extending into the openings when the cage is in the expanded position, the material removing element being positioned beneath the cage and being configured to be movable along the inner surface of the cage to remove the material extending into the openings.

2. The device of claim 1, further comprising:
   a collapsible bag positioned to receive the material removed by the material removing element.

3. The device of claim 2, wherein:
   the bag is coupled to the material removing element.

4. A device for removing material from a vessel wall at a vascular site, comprising:
   a sheath;
   an expandable cage movable from a collapsed position to an expanded position, the cage forming a plurality of openings in the expanded position, the cage being configured such that when the cage is in the expanded position at the vascular site material from the vessel wall extends from the vessel wall into the openings, the expandable cage having an inner surface which defines a cavity, the expandable cage being contained within the sheath in the collapsed position so that the sheath holds the cage in the collapsed position, the cage being releasable so that the cage may be left within the patient;
   the sheath being retractable relative to the cage to expose the cage and permit the cage to expand; and
   a material removing element positioned within the cage cavity to remove material from the vessel wall extending into the openings, the material removing element being positioned beneath the cage and being configured to be movable along the inner surface of the cage to remove the material extending into the openings.

5. The device of claim 4, wherein:
   the cage has rigidly connected elements which form the openings, the rigidly connected elements being deformed when moved from the expanded position to the collapsed position.

6. The device of claim 4, wherein:
   the rigidly connected elements are deformed within an elastic range when moving from the expanded position to the collapsed position.

7. The device of claim 4, further comprising:
   a collapsible bag positioned to receive the material removed by the material removing element.

8. The device of claim 7, wherein:
   the bag is coupled to the material removing element.

9. The device of claim 4, wherein:
   the cage forms 2-10 openings.

10. The device of claim 4, wherein:
    the openings have a length of at least 1 mm.

11. The device of claim 4, wherein:
    the openings have a size of at least 0.5 mm.

* * * * *